(12) United States Patent
Pillai et al.

(10) Patent No.: US 8,124,123 B2
(45) Date of Patent: Feb. 28, 2012

(54) CONTROLLED RELEASE AZITHROMYCIN SOLID DOSAGES FORMS

(75) Inventors: Radhakrishnan Pillai, Santa Rosa, CA (US); Pramod Sarpotdar, San Diego, CA (US); David W. Osborne, Santa Rosa, CA (US); Gordon J. Dow, Santa Rosa, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 278 days.

(21) Appl. No.: 12/002,417

(22) Filed: Dec. 17, 2007

(65) Prior Publication Data

US 2009/0060994 A1  Mar. 5, 2009

Related U.S. Application Data

(60) Provisional application No. 60/967,504, filed on Sep. 5, 2007.

(51) Int. Cl.
*A61K 9/54* (2006.01)
*A61K 9/52* (2006.01)
*A61K 31/7052* (2006.01)
*A61K 9/28* (2006.01)
*A61K 9/22* (2006.01)
*A61P 31/00* (2006.01)

(52) U.S. Cl. ........ 424/458; 424/457; 424/463; 424/468; 424/474; 514/29

(58) Field of Classification Search .................. None
See application file for complete search history.

(56) References Cited

U.S. PATENT DOCUMENTS

| 4,474,768 A | * | 10/1984 | Bright | 514/29 |
| 5,605,889 A | * | 2/1997 | Curatolo et al. | 514/29 |
| 7,108,865 B2 | * | 9/2006 | Curatolo et al. | 424/489 |

FOREIGN PATENT DOCUMENTS

WO  WO 2006/067576 A1  6/2006

OTHER PUBLICATIONS

Fiese et al. (Journal of Antimicrobial Chemotherapy (1990) 25, Suppl. A, 39-47).*
Pfizer Central Research, Biopharmaceutics Review—FDA New Drug Application (NDA) 50,711, Azithromycin Tablet (Zithromax) (1994).

* cited by examiner

*Primary Examiner* — David J Blanchard
*Assistant Examiner* — Garen Gotfredson
(74) *Attorney, Agent, or Firm* — Howard Eisenberg, Esq.

(57) ABSTRACT

A solid dosage form for oral administration comprising azithromycin in an amount below that which causes gastrointestinal side effects, which dosage form is a controlled release dosage form.

48 Claims, 3 Drawing Sheets

CONTROLLED RELEASE AZITHROMYCIN SOLID DOSAGES FORMS

This Application claims priority from pending U.S. Provisional Patent Application Ser. No. 60/967,504, filed Sep. 5, 2007.

FIELD OF THE INVENTION

The invention pertains to the field of orally administered dosage forms containing antimicrobial pharmaceutical agents and particularly to solid oral dosage forms of azithromycin.

BACKGROUND OF THE INVENTION

Azithromycin, a broad spectrum antibiotic derived from erythromycin A, is the generic name for 9-deoxo-9a-aza-9a-methyl-9a-homoerythromycin A. It was independently discovered by Bright, U.S. Pat. No. 4,474,768 and Kobrehel, U.S. Pat. No. 4,517,359, where it was referred to by the name of N-methyl-11-aza-10-deoxo-10-dihydroerythromycin A. Bright and Kobrehel disclosed azithromycin as a hygroscopic monohydrate form. Allen, U.S. Pat. No. 6,268,489, discloses a non-hygroscopic dihydrate form of azithromycin. Both the monohydrate form and the dihydrate form are effective in treating bacterial infections when administered systemically.

The presence of food in the GI tract can significantly influence the bioavailability of an orally administered drug. If the bioavailability of a drug is affected due to the presence of food in the GI tract, the drug is said to exhibit a "food effect". It has been reported that certain orally administered formulations of azithromycin may exhibit a food effect when administered following the ingestion of a meal. Curatolo, U.S. Pat. No. 5,605,889, discloses that orally administered capsule dosage forms of azithromycin exhibit a food effect but that tablet dosage forms, because they disintegrate rapidly following ingestion, do not exhibit a food effect. The azithromycin tablets, which do not exhibit a food effect, may contain a polymeric film coating that is soluble in the stomach, to provide ease of swallowing and an elegant appearance.

Pfizer Inc., the manufacturer of Zithromax® brand of azithromycin capsules and tablets, presented data in a 1995 Biopharmaceutics Review submitted to the Food and Drug Administration (FDA) in association with New Drug Application (NDA) 50,711 that established that the food effect of orally administered azithromycin is dependent on formulation. The data established that azithromycin orally administered in the form of a capsule exhibited a food effect but that azithromycin administered in the form of a tablet exhibited no food effect.

The data establishing a lack of food effect of azithromycin tablets in both the Curatolo, U.S. Pat. No. 5,605,889 and in association with NDA 50,711 was obtained following administration of a dosage of 500 mg (2×250 mg tablets) to each subject. The 500 mg azithromycin dosage was administered according to FDA protocol as a crossover study in which the azithromycin was administered to subjects on a first occasion either following an overnight fast or following a standard meal high in fat content. After a fifteen day washout period, the subjects were administered the azithromycin under the alternate treatment conditions. Under these conditions, it was established that the bioavailability of azithromycin administered as two 250-mg tablets was not significantly changed by a high fat diet and further established that the 250 mg tablet may be administered without restrictions relative to the ingestion of meals.

No studies have been reported concerning the presence or absence of a food effect associated with azithromycin tablets containing an amount of azithromycin less than 250 mg.

Curatolo, U.S. Pat. No. 7,108,865, discloses that orally administered azithromycin produces a dose-related incidence of gastrointestinal side effects. Side effects including diarrhea/loose stools, abdominal pain, nausea, and vomiting were reported with administration of a single dose of 1000 mg of azithromycin and also with 1500 mg of azithromycin administered over a 5 day course of azithromycin therapy consisting of 500 mg on day 1, followed by 250 mg on each of days 2 through 5. Curatolo further discloses a controlled release dosage form that decreases the exposure of the duodenum to high doses of azithromycin permits the administration of high doses of azithromycin, such as between 1 and 7 grams, with reduced incidence of side effects.

Curatolo, U.S. Pat. No. 7,108,865, does not disclose an isolated dosage of azithromycin of less than 750 mg and discloses the administration of azithromycin tablets of 250 mg only as a sequence of administrations in order to obtain a total dosage of at least 1 gram. Curatolo does not pertain to the oral administration of azithromycin at dosages below that which cause gastrointestinal side effects.

Appel, et al, WO 2006/067576, discloses a multiparticulate azithromycin tablet. The azithromycin tablet contains a multiplicity of "cores", each of which contains azithromycin and each of which is coated with an enteric coating. The coated multiparticulates are assembled into a tablet that, upon oral administration, rapidly disintegrates to allow the coated multiparticulates to be dispersed. In this way, the object of the patent, to obtain an enterically coated multiparticulate controlled release azithromycin dosage form that decreases, relative to currently available immediate release dosage forms that deliver an equivalent dose, the incidence and/or severity of GI side effects.

Appel does not pertain to oral dosage forms of azithromycin that contain an amount of azithromycin below that which causes gastrointestinal side effects.

Regarding capsule oral dosage forms, both Curatolo, U.S. Pat. No. 5,605,889, and the 1995 Biopharmaceutics Review submitted to the Food and Drug Administration (FDA) in association with New Drug Application (NDA) 50,711 disclose a food effect. However, such food effect in capsules was established with capsules containing 250 mg of azithromycin. The presence of food effect with capsules was not studied with lower amounts of azithromycin.

DESCRIPTION OF THE INVENTION

Figure 1:
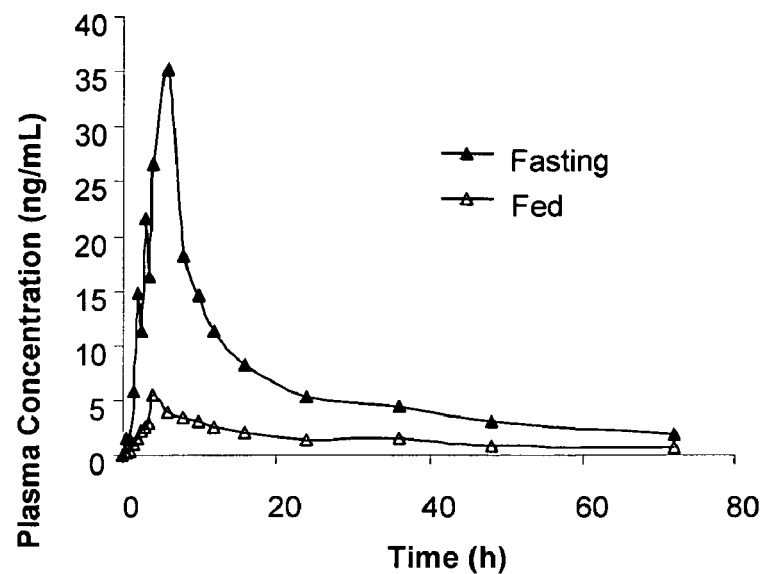
FIG. 1 is a graph comparing plasma concentration of azithromycin over time following a single oral administration to fed subjects and to the same fasting subjects of a prior art non-controlled release capsule containing azithromycin in an amount below that which causes gastrointestinal side effects.

It has been unexpectedly discovered that dosage forms, such as tablets, containing azithromycin in an amount below that which causes gastrointestinal side effects exhibit a food effect when orally administered to an individual following ingestion of a meal. This discovery is especially surprising in view of the disclosures of Curatolo, U.S. Pat. No. 5,605,889, and of Food and Drug Administration (FDA) New Drug Application (NDA) 50,711 that provide data to show that tablets containing azithromycin for oral administration do not exhibit a food effect. Such data, however, which also showed that capsules containing azithromycin exhibit a food effect, was obtained with such solid oral dosage forms containing azithromycin in an amount that is known to cause gastrointestinal side effects Thus, the inventors have discovered a previously unidentified problem concerning the oral administration of dosage forms of azithromycin, such as tablets. Because tablets containing azithromycin in an amount below that which causes gastrointestinal side effects exhibit a food effect when administered following the ingestion of a meal, the bioavailability of such tablets is markedly reduced. Further, because such administered amount of azithromycin is by necessity a low amount, the reduction of bioavailability due to this food effect may be such as to represent the loss of a significant percentage of the azithromycin contained within the tablet and, therefore, the effectiveness of the azithromycin contained within the tablet may be significantly decreased. Accordingly, when administering tablets containing such amounts of azithromycin, it is desirable to provide the administered azithromycin in a tablet dosage form that reduces this food effect.

Moreover, because azithromycin capsules have been recognized to exhibit a food effect, but this was only recognized in capsules containing an amount of azithromycin above that which causes gastrointestinal side effects, the present discovery of food effect at low dosages of azithromycin is applicable to capsules as well as tablets. Accordingly, when administering any solid oral dosage form, including capsules, containing such amounts of azithromycin, it has been discovered that it is desirable to provide the administered azithromycin in a capsule or other dosage form that reduces this food effect.

The dosage forms of the invention containing a dosage of azithromycin below that which causes gastrointestinal side effects provide a controlled release of azithromycin that significantly reduces the food effect that would otherwise occur following the administration of such dosage forms of azithromycin to a non-fasting individual.

Additionally, azithromycin is chemically unstable at pH 1, the pH that is found in stomach contents following a meal. Typically a tablet or capsule containing azithromycin remains in the stomach for about one hour, during which time approximately one third of azithromycin released into the stomach may be destroyed by the low pH environment. In the provisional patent application from which this application claims priority, it is reported that azithromycin is effective in treating skin diseases such as acne at dosages below that which cause gastrointestinal side effects. At such low levels of azithromycin, gastric degradation of azithromycin under fed conditions may become highly significant. The present invention provides dosage forms containing such low amounts of azithromycin and further provides a controlled release functionality so that sufficient amounts of azithromycin are protected from degradation in the stomach and are available for treatment of a bodily disorder.

The term "azithromycin" includes all forms of azithromycin that may be administered therapeutically to an individual for treatment of a disorder that responds to treatment with azithromycin. Such forms of azithromycin include all amorphous and crystalline forms of azithromycin, including all co-crystals, co-precipitates, polymorphs, isomorphs, clathrates, salts, solvates, and hydrates of azithromycin, as well as anhydrous azithromycin, or a combination of forms. Specific examples of azithromycin include dihydrate azithromycin, which is disclosed in Allen, U.S. Pat. No. 6,268,489, and monohydrate azithromycin, which is disclosed in Bright, U.S. Pat. No. 4,474,768 and Kobrehel, U.S. Pat. No. 4,517,359.

The amount of azithromycin below that which causes gastrointestinal side effects is not precisely defined in the prior art. However, azithromycin has been shown to have a dose dependent incidence of side effects. Because the incidence of side effects due to the oral administration of azithromycin at any dose level can never be determined to be zero, for purposes of this patent application, the amount of azithromycin below that which causes gastrointestinal side effects is defined herein as a dosage form for oral administration containing less than 250 mg.

The term "tablet" means a solid pharmaceutical dosage form containing a drug substance with or without suitable diluents and prepared by compression or molding techniques. Examples of tablets include compressed tablets, multiparticulate tablets, multiple compressed tablets, coated tablets, matrix tablets, osmotic tablets, and caplets.

The term "multiparticulate tablet" means a tablet dosage form containing a multiplicity of coated or uncoated particles containing azithromycin whose totality represents the intended therapeutic dosage of azithromycin. Examples of types of multiparticulate tablets that may be configured so as to be suitable for the tablet of the present invention are disclosed in Appel, PCT Publication WO 2006/067576.

The term "capsule" means a dosage form that contains a plurality of solid particulates that are encapsulated within a shell, which is typically made of gelatin but may be made of other materials. The shell of the capsule disintegrates following digestion to release the particulate contents. The particulates within the capsule are not compressed together to form a tablet. If a capsule contains a multiplicity of particles that are compressed to form a solid mass, such dosage form is considered to be a tablet within a capsule.

One type of capsule known in the prior art is a capsule containing other than a drug in the form of multiple particles. Such capsules include both hard shell capsules and soft shell, such as softgel, capsules. As used herein, these types of capsules refer to a hard shell or a one-piece, sealed, soft shell, typically made of gelatin but which may also be made of other film-forming materials, that contains within the shell a liquid in the form of a solution, a suspension, or a semi-solid gel or paste. Because such capsules, upon degradation of the shell, release their contents in the form of a liquid, which release is more closely related to the rapid disintegration of a tablet rather than the release of multiple particles such as from a capsule, these tend to act as tablets. Therefore, the present invention, as it pertains in particular to enteric-coated tablets, pertains likewise to enteric-coated capsules containing azithromycin in solution, suspension, or as a semi-solid gel or paste.

The term "food effect" refers to a change in bioavailability of an orally administered drug when ingested following a meal compared to the bioavailability of the administered drug when ingested following a period of fasting. The presence of a change in bioavailability may be determined by comparing the area under the curve (AUC) pharmacokinetics of a drug when administered following a meal ($AUC_{fed}$) and when administered following a period of fasting ($AUC_{fasting}$). The AUC is the area under the curve in a plot of concentration of azithromycin in plasma over time following a single administration of a dosage form containing azithromycin. $AUC_{0-72}$ refers to the area under the curve of azithromycin in plasma from a period beginning at the administration of a dosage form containing azithromycin until 72 hours following the administration. In this specification, a drug or a dosage form containing a drug is understood to exhibit a significant food effect when the $AUC_{fed}/AUC_{fasting} < 0.75$ when averaged in at least 6 subjects in a crossover design with a washout period of at least 10 days.

In one embodiment, the invention is an orally administrable dosage form, such as a tablet or a capsule, containing azithromycin in an amount below that which causes gastrointestinal side effects which dosage form yields a controlled release of azithromycin following ingestion. In a preferred embodiment, the dosage form, such as the tablet or capsule, includes an enteric coating that provides this controlled release.

The term "controlled release" when referring to a dosage form containing azithromycin means that the release of azithromycin from the dosage form occurs at a rate sufficiently slow so that the food effect of the azithromycin contained in the dosage form is reduced compared to a comparable immediate release dosage form, which may be referred to as "sustained release", or that the majority of the azithromycin in the dosage form is released in a portion of the gastrointestinal tract distal to the stomach, which may be referred to as "delayed release".

The term "enteric coating" means a coating, typically containing a polymer, that is situated on a solid dosage form, such as tablet or capsule, and that causes the majority of a drug contained in the dosage form to be released in a portion of the gastrointestinal tract distal to the stomach. Preferably, the enteric coating of the invention causes at least 80% of the drug contained in the dosage form to be released distal to the stomach. More preferably at least 90% of the drug is released distal to the stomach. Most preferably, at least 95% of the drug is released distal to the stomach. Typically, the enteric coating is a pH sensitive coating that is substantially insoluble at a pH found in the stomach and which is substantially more soluble at a pH found in the small intestine.

Examples of enteric coatings include polyacrylamides, phthalate derivatives such as acid phthalates of carbohydrates, amylose acetate phthalate, cellulose acetate phthalate, other cellulose ester phthalates, cellulose ether phthalates, hydroxypropylmethylcellulose phthalate, methylcellulose phthalate, hydroxypropylcellulose phthalate, hydroxypropylethylcellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinylacetate phthalate copolymer, cellulose acetate trimellitate, hydroxypropyl methylcellulose acetate succinate, cellulose acetate succinate, carboxymethyl cellulose, carboxyethyl cellulose, carboxymethylethyl cellulose, styrene and maleic acid copolymers, polyacrylic acid derivatives such as acrylic acid and acrylic ester copolymers, polymethacrylic acid and esters thereof, polyacrylic methacrylic acid copolymers, shellac, vinyl acetate and crotonic acid copolymers, and mixtures thereof. Preferred enteric coatings include methacrylic copolymers sold under the tradename EUDRAGIT® (Evonik Industries AG, Essen, Germany). A most preferred enteric coating is Eudragit L30D-55, a methacrylic acid-ethyl acrylate copolymer, which is a 30% aqueous dispersion that dissolves at pH above 5.5.

Methods for applying coatings, including enteric polymer coatings, to solid dosage forms such as tablets and capsules are well known in the art. Typical coating methods for applying enteric polymers include fluidized bed and side vented pan coating processes. In these processes, a coating formulation containing an enteric polymer or blend, and possibly including additional materials such as plasticizers and fillers, is applied, such as by use of spray nozzles, onto the dosage forms. During this application process, the dosage form is fluidized, such as with heated air or by agitation in a rotating pan, with or without heated air, to prevent agglomeration and to facilitate the drying of the polymer film. Such processes, as well as other processes known in the art, result in a uniform film being applied to the surface of the dosage form. The rate of release of the active ingredient is controlled by factors such as the physico-chemical properties of the polymers constituting the coating, the thickness of the coating, the presence of additives in the coating, the solubility of the active ingredient, and the acidity or alkalinity of the extracting medium.

Particles, such as granules, may be coated, such as by the methods described above and such particles may be compacted into a multiparticulate controlled release tablet. Alternatively, such particles may be loaded into a capsule to provide a multiparticulate controlled release capsule.

A controlled release tablet formulation containing azithromycin may also be in the form of a buoyant tablet (i.e., a tablet that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules may then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Alternative controlled release tablet formulations may use the OROS® technology developed by Alza Corp. (Mountain View, Calif.). In that system, the azithromycin formulation is enclosed, at least partially, in a semipermeable membrane that allows water to enter and slowly push drug out through a small opening due to osmotic effects. See, e.g., U.S. Pat. Nos. 3,995,631; 3,977,404; and 5,156,850.

Examples of types of controlled release devices that are suitable for the controlled release tablet of the invention containing azithromycin are disclosed in Chopra, U.S. Pat. No. 6,960,357; Chen, U.S. Pat. No. 5,419,917; Mulligan, U.S. Pat. No. 5,128,142; Calanchi, U.S. Pat. No. 5,047,248; Dumitriu, U.S. Pat. No. 5,858,392; Odidi, U.S. Pat. No. 6,893,661; Lenaerts, U.S. Pat. No. 6,607,748; Baichwal, U.S. Pat. No. 6,709,677; Conte, U.S. Pat. No. 5,422,123; Rudnic, U.S. Pat. No. 5,484,608; and Cremer, U.S. Pat. No. 6,238,698. Preferred examples of controlled release devices that are suitable for the controlled release tablet of the invention are disclosed in Curatolo, U.S. Pat. No. 7,108,865.

The amount of azithromycin in the dosage form, such as the tablet, is an amount between 1 mg and less than 250 mg. For example, the dosage form may contain 5, 10, 25, 30, 40, 50, 60, 75, 80, 100, 120, 125, 150, 175, or 200 mg. Preferably the amount of azithromycin in the dosage form is 200 mg or less, more preferably 150 mg or less, and most preferably 100 mg or less. In a particularly preferred embodiment, the amount of azithromycin in the dosage form is 80 mg or less, such as 80, 60, or 30 mg.

The dosage form of the invention may contain, in addition to azithromycin, excipients that are commonly used in the manufacture of oral pharmaceutical dosage forms. Examples of such excipients include inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Examples of other pharmaceutically acceptable excipients include colorants, flavoring agents, plasticizers, humectants, and buffering agents.

The dosage form of the invention, such as the tablet of the invention, may include a non-enteric coating, such as a film-coating to provide ease of swallowing and an elegant appearance. Many polymeric film-coating materials are known in the art. A preferred film-coating material is hydroxypropylmethylcellulose (HPMC). HPMC may be obtained commercially, for example from Colorcon Inc. (West Point, Pa.), in coating formulations containing excipients which serve as coating aids, under the registered trademark OPADRY®. Opadry formulations may contain lactose, polydextrose, triacetin, polyethyleneglycol, polysorbate 80, titanium dioxide, and one or more dyes or lakes. Other suitable film-forming polymers also may be used herein, including, hydroxypropyl cellulose, and acrylate-methacrylate copolymers.

The dosage form may contain another drug, in addition to azithromycin. The two drugs of the formulation may be mixed together in the dosage form, or may be partitioned. For example, the azithromycin may be contained on the inside of the dosage form and the second drug is on the outside, such that a substantial portion of the second drug is released prior to the release of the azithromycin.

As known in the art, tablet blends may be dry-granulated or wet granulated before tableting. Alternatively, tablet blends may be directly compressed or slugged. The choice of processing approach depends upon the properties of the drug and chosen excipients, for example particle size, blending compatibility, density and flowability. In a preferred embodiment, a powder containing azithromycin is granulated. The azithromycin may be granulated with or without additional intragranular excipients and then, if desired, additional excipients may be added extragranularly. In addition, tablets may also be coated with a coating that exhibits little or no effect on or interference with tablet dissolution to assure ease of swallowing or to provide an elegant appearance.

Alternatively, granules made by processes such as dry or wet granulation may be loaded into capsules. The individual granules may be coated, such as with an enteric coating, to provide for a multiparticulate controlled release capsule. Alternatively, or in addition to the coating of the individual particles, a coating, such as an enteric coating, may be applied to the surface of the capsule shell.

Any excipients used in making the dosage form of the invention should be pharmaceutically acceptable and compatible with the azithromycin in the dosage form. The azithromycin in the dosage form may be in any one or more pharmaceutically acceptable forms, including crystalline and amorphous forms of azithromycin, such as azithromycin dihydrate, azithromycin monohydrate, or a combination. In addition, it is preferred that the dosage form should be physically and chemically stable for a commercially reasonable period of time, for example when stored at room temperature for 18 months.

In a preferred embodiment, the dosage form of the invention containing azithromycin in an amount below that which causes gastrointestinal side effects is a controlled release dosage form, such as a tablet, that releases not more than 50% of the azithromycin contained therein at pH 1, the pH typically found in the stomach, within one hour at 37° C. The amount of release of azithromycin is determined as follows. The testing is conducted in a USP Type II (paddle) equipment. A dissolution medium is maintained at 37° C.±0.5° C. The dosage form containing azithromycin is immersed in 900 ml of 0.1N hydrochloric acid while mixing at 75 rpm. At the end of one hour, the dosage form is removed from the medium and analyzed for content of azithromycin by HPLC. The amount of azithromycin released is then calculated by subtracting from the average initial azithromycin in the dosage form the amount retained in the dosage form after exposure to the acidic medium.

Preferably, the dosage form releases not more than 25% of the azithromycin contained therein within one hour at pH 1 at 37° C. More preferably, the dosage form releases not more than 10% of the azithromycin contained therein within one hour at pH 1 at 37° C. Most preferably, the dosage form releases not more than 5% of the azithromycin contained therein within one hour at pH 1 at 37° C. Dosage forms of the invention thus release the majority of the azithromycin contained therein in the portion of the gastrointestinal tract distal to the stomach. It is immaterial to the present invention where within the gastrointestinal tract distal to the stomach the majority of the azithromycin is released, so long as a pharmaceutically effective amount of the azithromycin contained in the dosage form is released for absorption as opposed to being excreted in feces. Thus, in addition, the dosage form releases at least 50% of the azithromycin contained therein within 10 hours at pH 6.0 or higher at 37° C. Preferably, the dosage form releases at least 75% of the azithromycin contained therein within 10 hours at pH 6.0 or higher at 37° C. Most preferably, at least 90% of the azithromycin is released within 10 hours at pH 6.0 or higher at 37° C.

In a preferred embodiment, the dosage form of the invention containing azithromycin in an amount below that which causes gastrointestinal side effects is a controlled release dosage form, such as a tablet or capsule, which preferably is an enteric coated tablet or capsule, that provides an $AUC_{fed}/AUC_{fasting}$ for azithromycin following administration to an individual following a meal that is, on average, at least 33% higher than the $AUC_{fed}/AUC_{fasting}$ obtained from an otherwise identical dosage and dosage form that is not a controlled release dosage form in identical dose, such as lacking the enteric coating, that is administered in this manner. Preferably, the $AUC_{fed}/AUC_{fasting}$ obtained with the dosage form of the invention is at least 50% higher than that obtained with a similar dosage form that is not a controlled release dosage form. More preferably, the $AUC_{fed}/AUC_{fasting}$ obtained with the dosage form of the invention is at least 75% higher. Most preferably, the $AUC_{fed}/AUC_{fasting}$ obtained with the dosage form of the invention is at least 100% higher.

In another embodiment, the invention is a method for making a controlled release dosage form, such as a tablet, for oral administration containing azithromycin in an amount that is below that which causes gastrointestinal side effects.

According to this embodiment of the invention, an amount of azithromycin that is less than that which causes gastrointestinal side effects is combined with one or more pharmaceutical excipients, the combination is optionally formed into granules, and the combination, in the form of a powder or of granules, is pressed or compacted into a solid form or is encapsulated within a shell. The solid form may be a tablet or may be one of a multiplicity of multiparticulates that are to be pressed or compacted into a unitary tablet or encapsulated within a shell.

Depending on the nature of the controlled release mechanism that is employed, the controlled release mechanism may be combined with the azithromycin and the excipients before or after the compaction or pressing into the solid form or before or after encapsulation within a shell. For example, as discussed above, if the controlled release tablet is a buoyant tablet, a hydrocolloid is mixed with the azithromycin and excipients, and this mixture is then granulated and compressed into a solid form. Alternatively, if the controlled release tablet contains an enteric coating, the coating is applied following compression of the azithromycin and excipients into a solid form. Individual particles may be enteric coated before encapsulation within a shell. Alternatively, a capsule shell containing within individual particles containing azithromycin may be enteric coated.

In another embodiment, the invention is a method for treating a bodily disorder that may be ameliorated by the oral administration of azithromycin in a dosage that is below that which causes gastrointestinal side effects. In accordance with this method of the invention, one or more controlled release dosage forms of the invention containing azithromycin is administered to an individual suffering from a bodily disorder that is effectively treated with an amount of azithromycin that is below that which causes gastrointestinal side effects, wherein the total amount of azithromycin administered to the individual in the one or more dosage forms on any one day of treatment in which azithromycin is administered is below that which causes gastrointestinal side effects.

If desired, the treatment regimen of the invention may be preceded by one or more loading doses of azithromycin that is or are above the amount that causes gastrointestinal side effects. Such loading dose or multiplicity of loading doses is not preferred, because loading doses are not typically necessary and increase the likelihood that an individual will experience gastrointestinal side effects. However, the utilization of such loading dose or doses does not take the azithromycin treatment regimen out of the scope of the present invention so long as the loading dose regimen is followed by the method of treatment according to the present invention.

In accordance with this method of the invention, it is preferred that the total amount of azithromycin administered in one day to an individual is 200 mg or less. It is more preferred that the amount is 150 mg or less and even more preferred that it is 125 mg or less. It is particularly preferred that the amount is 100 mg or less and most particularly preferred that it is 80 mg or less. Examples of particularly preferred embodiments are single day administrations of 60, 40, or 30 mg or less.

The invention is further illustrated by the following non-limiting examples.

EXAMPLE 1

Food Effect with Azithromycin Capsules

The effect of food on the serum concentrations of azithromycin following oral administration of a single dose of a non-controlled release capsule containing 80 mg of azithromycin was assessed in six subjects in a crossover study. On day 1 of the study, each of the subjects was administered the capsule either following a 10 hour overnight fast or after eating a standardized meal high in fat and caloric content. On day 15, the subjects were administered a single dose of a capsule containing 80 mg of azithromycin under the alternate treatment condition. Blood was taken from each subject at intervals up to 72 hours following each dose in order to determine the pharmacokinetic parameter AUC (area under the curve). The results are shown in tabular form in Table 1 and graphically in FIG. 1.

TABLE 1

| Subject | $AUC_{0-72}$ Fasting (ng · hr/ml) | $AUC_{0-72}$ Fed (ng · hr/ml) | $AUC_{fed}/AUC_{fasting}$ | % decrease in bioavailability |
|---|---|---|---|---|
| 1 | 318 | 183 | 0.58 | 42 |
| 2 | 671 | 119 | 0.18 | 82 |
| 3 | 534 | 173 | 0.32 | 68 |
| 4 | 498 | 44 | 0.09 | 91 |
| 5 | 687 | 97 | 0.14 | 86 |
| 6 | 129 | 27 | 0.21 | 79 |
| Average | 473 | 107 | 0.25 | 75 |

Table 1 and FIG. 1 show that a significant food effect exists following oral administration of capsules containing azithromycin at a dosage below that which causes gastrointestinal side effects. When a capsule containing 80 mg of azithromycin was administered following a meal, the pharmacokinetic parameter $AUC_{0-72}$ was reduced, on average, to 25% of the $AUC_{0-72}$ compared to when the azithromycin capsule was administered following a period of fasting. Thus, on average, 75% less of the azithromycin in the 80 mg capsule is bioavailable to a fed individual compared to that which is bioavailable to a fasting individual.

EXAMPLE 2

Food Effect with Azithromycin Tablets

The study of Example 1 was repeated in six subjects except that the 80 mg azithromycin was administered in a non-controlled release tablet, rather than a capsule. The results are shown in tabular form in Table 2 and graphically in FIG. 2.

TABLE 2

| Subject | $AUC_{0-72}$ Fasting (ng · hr/ml) | $AUC_{0-72}$ Fed (ng · hr/ml) | $AUC_{fed}/AUC_{fasting}$ | % decrease in bioavailability |
|---|---|---|---|---|
| 7 | 666 | 41 | 0.06 | 94 |
| 8 | 354 | 292 | 0.82 | 18 |
| 9 | 600 | 184 | 0.31 | 69 |
| 10 | 924 | 305 | 0.33 | 67 |
| 11 | 1402 | 401 | 0.29 | 71 |
| 12 | 1033 | 408 | 0.40 | 60 |
| Average | 830 | 272 | 0.37 | 63 |

Figure 2:
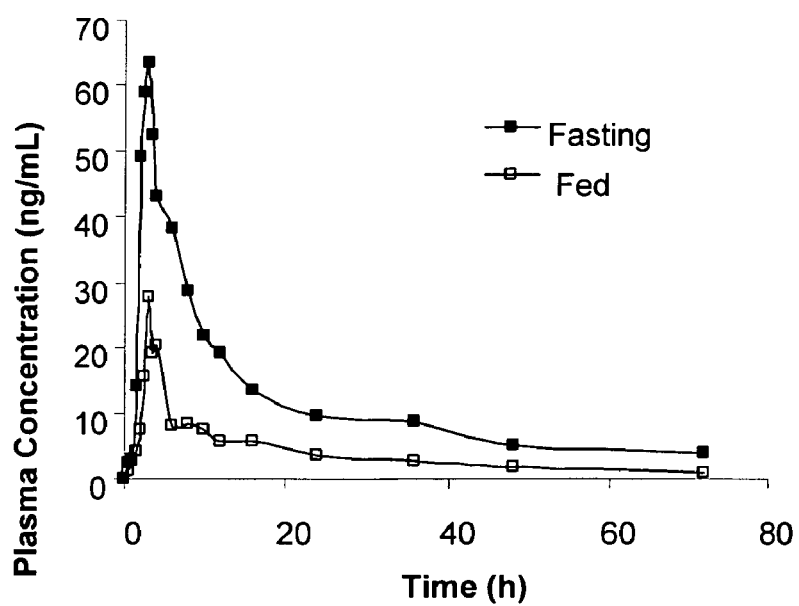
FIG. 2 is a graph comparing plasma concentration of azithromycin over time following a single oral administration to fed subjects and to the same fasting subjects of a prior art non-controlled release tablet containing azithromycin in an amount below that which causes gastrointestinal side effects.

Table 2 and FIG. 2 show that a significant food effect exists following oral administration of tablets containing azithromycin at a dosage below that which causes gastrointestinal side effects. When a tablet containing 80 mg of azithromycin was administered following a meal, the pharmacokinetic parameter $AUC_{0-72}$ was reduced, on average, to 37% of the $AUC_{0-72}$ compared to when the azithromycin tablet was administered following a period of fasting. Thus, on average, 63% less of the azithromycin in the 80 mg tablet is bioavailable to a fed individual compared to that which is bioavailable to a fasting individual. These results are especially surprising in view of the prior art that teaches the lack of a food effect when azithromycin is orally administered in the form of a tablet containing azithromycin in an amount known to cause gastrointestinal side effects (250 mg or more).

EXAMPLE 3

Food Effect with Azithromycin Enteric-Coated Tablets

The study of Examples 1 and 2 was repeated in six subjects except that the 80 mg azithromycin was administered in an enteric-coated tablet. The results are shown in tabular form in Table 3 and graphically in FIG. 3.

TABLE 3

| Subject | $AUC_{0-72}$ Fasting (ng · hr/ml) | $AUC_{0-72}$ Fed (ng · hr/ml) | $AUC_{fed}/AUC_{fasting}$ | % decrease in bioavailability |
|---|---|---|---|---|
| 13 | 633 | 613 | 0.97 | 3 |
| 14 | 552 | 494 | 0.89 | 11 |
| 15 | 347 | 449 | 1.29 | −29 |
| 16 | 685 | 507 | 0.74 | 26 |
| 17 | 673 | 202 | 0.30 | 70 |
| 18 | 511 | 523 | 1.02 | −2 |
| Average | 567 | 465 | 0.87 | 13 |

Figure 3:
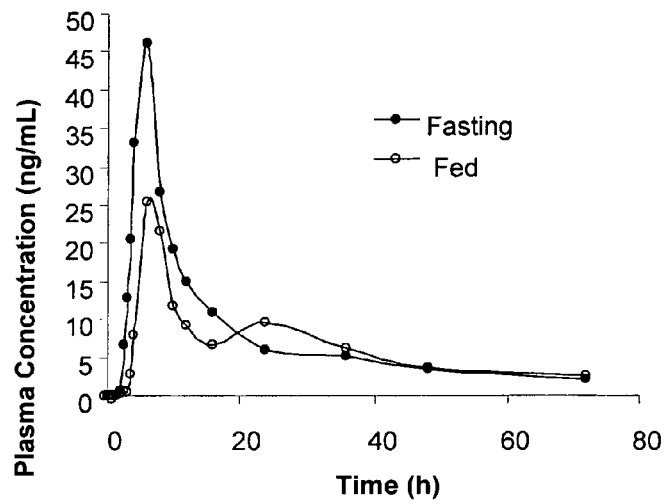
FIG. 3 is a graph comparing plasma concentration of azithromycin over time following a single oral administration to fed subjects and to the same fasting subjects of an enteric-coated tablet of the invention containing azithromycin in an amount below that which causes gastrointestinal side effects.

Table 3 and FIG. 3 show a significant decrease in food effect following oral administration of an enteric-coated dosage form containing azithromycin at a dosage below that which causes gastrointestinal side effects compared to an otherwise similar immediate release dosage form. When a controlled release enteric-coated tablet containing 80 mg of azithromycin was administered following a meal, the pharmacokinetic parameter $AUC_{0-72}$ was reduced, on average, to 87% of that obtained following administration after a period of fasting. Thus, on average, only 13% less of the azithromycin in the controlled release 80 mg tablet is bioavailable to a fed individual compared to that which is bioavailable to a fasting individual.

As summarized in Table 4, the bioavailability ($AUC_{fed}/AUC_{fasting}$) obtained with the controlled release dosage form of Example 3 compares favorably with the values obtained with non-enteric coated capsules or tablets from Examples 1 and 2, from which the average bioavailability was reduced to 23% and 37%, respectively, while it was 87% with the controlled release dosage form of the invention. Thus, two-thirds to three-quarters of the administered azithromycin dosage was lost from the non-controlled release dosage forms and only about one eighth of the azithromycin dosage was lost from the controlled release dosage form of the invention.

TABLE 4

| Dosage Form | $AUC_{fed}/AUC_{fasting}$ | % Increase in $AUC_{fed}/AUC_{fasting}$ of enteric coated tablet compared to immediate release dosage form |
|---|---|---|
| Enteric Coated Tablet (Example 3) | 0.87 | — |
| Immediate Release Tablet (Example 2) | 0.37 | 135.00 |
| Immediate Release Capsule (Example 1) | 0.25 | 248.00 |

The data of Examples 1 to 3 establish that a food effect, as determined by measurement of AUC, occurs with azithromycin when administered at doses lower than that which causes gastrointestinal side effects. The data further establish that the magnitude of the food effect is markedly decreased by administering such doses of azithromycin in a controlled release dosage form. Thus, the controlled release dosage forms provide a much higher percentage bioavailability of the administered azithromycin when administered to subjects under fed conditions.

EXAMPLE 4

Controlled Release Tablet Formulations

Controlled release enteric coated tablets containing an amount of azithromycin below that which causes gastrointestinal side effects were formulated as follows.

Azithromycin was combined with optional intragranular excipients, including a binder, a diluent, and a lubricant, sifting these ingredients, and mixing until a uniform blend was obtained. The mixture was then compacted into slugs which were then milled to form granules. Optional extragranular excipients, including a binder, a diluent, and a lubricant, were then added to the granules and the granules and this combination was mixed until the granules were evenly distributed in the extragranular excipients to form a lubricated blend. The lubricated blend was then compressed to form tablets using a commercially available tablet press. An optional subcoating was made by mixing together subcoating ingredients. The subcoating ingredients may also be used to make a film coating, if no further coating, such as an enteric coating, is applied on top of this coating. In order to apply the subcoating/film coating, the tablets were loaded in a perforated coating pan and the subcoating ingredients were added to the tablets to obtain about 3% coating buildup, after which the tablets were dried. An enteric coating solution was prepared by combining enteric coating ingredients and stirring until well blended. The tablets were coated with the enteric coating in a perforated coating pan and then allowed to dry. The enteric coating may also be applied directly onto the tablets, without an intermediate subcoating, if desired.

EXAMPLE 5

80 mg Enteric Coated Azithromycin Tablet

Enteric coated azithromycin tablets containing 80 mg of azithromycin were made according to Example 4. The tablets were formulated using pharmaceutical grade excipients and azithromycin according to the composition in Table 5.

TABLE 5

| INGREDIENTS | mg/tablet |
|---|---|
| Intragranular excipients | |
| Azithromycin (monohydrate) | 80.0 |
| Dibasic calcium phosphate | 31.62 |
| Croscarmellose sodium | 3.0 |
| Talc | 1.30 |
| Magnesium stearate | 1.00 |
| Extragranular excipients | |
| Dibasic calcium phosphate | 27.28 |
| Croscarmellose sodium | 3.0 |
| Talc | 1.3 |
| Magnesium stearate | 1.5 |
| Sub coating/Film coating | |
| Hydroxypropyl methylcellulose | 3.00 |
| PEG-6000 | 1.00 |
| Talc | 0.50 |
| Purified water | QS |
| Enteric coating | |
| Methacrylic Acid - ethyl acrylate copolymer | 40.33 |
| PEG-6000 | 1.612 |
| Talc | 1.209 |
| Polysorbate-80 | 0.080 |
| Purified water | QS |

EXAMPLE 6

Controlled Release Azithromycin Tablets

Additional controlled release enteric-coated tablets containing either 60 or 30 mg of azithromycin were made according to the method of Example 4. The quantitative composition and % w/w of pharmaceutical grade components per tablet are shown below in Table 6.

TABLE 6

| | 60 mg tablet | | 30 mg tablet | |
|---|---|---|---|---|
| Ingredients | mg/tablet | % wt/wt | mg/tablet | % wt/wt |
| Azithromycin (monohydrate) | 60 | 35.4 | 30 | 17.7 |
| Dicalcium phosphate | 75 | 44.2 | 108.3 | 63.9 |
| Croscarmellose sodium | 8 | 4.7 | 5.5 | 3.2 |
| Talc | 6.1 | 3.6 | 5.7 | 3.4 |
| Magnesium stearate | 2.6 | 1.5 | 2.2 | 1.3 |
| Hydroxypropyl methylcellulose | 3 | 1.8 | 3 | 1.8 |
| Polyethylene glycol 6000 | 2.6 | 1.5 | 2.6 | 1.5 |
| Methacrylic acid copolymer dispersion | 12.1 | 7.1 | 12.1 | 7.1 |
| Polysorbate 80 | 0.1 | 0.1 | 0.1 | 0.1 |
| Total | 169.5 | 100.0 | 169.5 | 100.0 |

EXAMPLE 7

Immediate and Controlled Release Capsules

Immediate release and controlled release capsules of azithromycin were prepared with Gelucire® 44/14 and Gelucire® 50/13 (Gattefosse, Gennevilliers, France), respectively. The Gelucire® products are semi-solid excipients well known in the pharmaceutical industry. They are mixtures of glycerol and PEG1500 esters of long fatty acids. Gelucire® 44/14 provides an immediate release formulation. Gelucire® 50/13 provides a controlled release formulation.

The Gelucire® was heated to about 65 to 75° C. and then an appropriate amount of azithromycin was added and mixed into the molten Gelucire® until the azithromycin was either dissolved or uniformly distributed. The mixture was cooled to about 40° C. and then was transferred into hard gelatin capsules. The loading of the azithromycin in the mixture was about 15% w/w, which provided an equivalent of 50 mg of azithromycin per capsule.

Dissolution studies were conducted with immediate and controlled release capsules and with a commercially available immediate release 250 mg azithromycin tablet cut in half (Teva Pharmaceuticals USA, North Wales, Pa.) in 0.1M phosphate buffer (pH 6.0) receptor medium at 37±0.5° C. using USP type I apparatus (basket) at 100 rpm. The samples were collected over 24 hours and analyzed for azithromycin using an HPLC method and reported as percent of dosage form content. The results are presented in FIG. 4.

Figure 4:
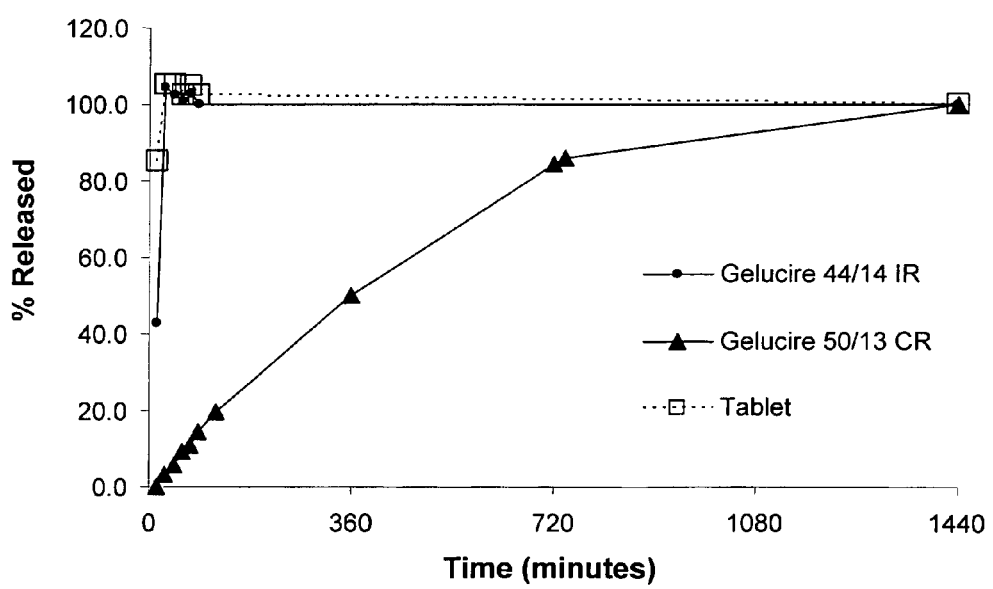
FIG. 4 is a graph comparing dissolution profiles of immediate release capsules (Gelucire 44/14 IR), controlled release capsules of the invention (Gelucire 50/13 CR), and immediate release tablets containing azithromycin.

As shown in FIG. 4, the immediate release capsules and tablets released all or essentially all of the azithromycin contained therein rapidly, within approximately 15 to 30 minutes. In contrast, the controlled release capsules released their azithromycin slowly. Only about 20% of the azithromycin in the controlled release capsules was released after 150 minutes. After 1 hour, less than 10% of the azithromycin from the controlled release capsules had been released.

EXAMPLE 8

Enteric Coated Capsules

Hard gelatin capsules containing 40 mg of azithromycin were enteric coated utilizing either cellulose acetate phthalate (CAP) or EUDRAGIT® 100-55 (Methacrylic Acid Copolymer, Type C, USP/NF). The compositions of the enteric coating materials are listed in Table 7.

TABLE 7

| Component | Function | Cellulose acetate phthalate coating | Eudragit coating |
|---|---|---|---|
| Triacetin (USP) | plasticizer | 1.5 | — |
| Polyethylene glycol (USP) | plasticizer | — | 1.5 |
| Acetone | solvent | 70.125 | 66.375 |
| Ethanol (USP, 190 proof) | solvent | 23.375 | 22.125 |
| Cellulose acetate phthalate | enteric coating polymer | 5 | — |
| Eudragit L 100-55 (USP/NF/EP) | enteric coating polymer | — | 10 |
| TOTAL | | 100.00 | 100.00 |

The dissolution properties of the CAP and EUDRAGIT® enteric coated capsules were evaluated using a triphasic dissolution medium using USP type I apparatus (baskets) at 50

RPM. The capsules were first immersed in 0.1 M HCl (pH about 1.0) and samples were taken for up to 2 hours (hours 0 to 2). Because the amount of azithromycin released in this medium was minimal, a 100 mL dissolution bath was used to increase concentration of the dissolved azithromycin (if any) in the medium. The capsules were then transferred to a dissolution bath containing 900 mL of 0.1M Citrate buffer, pH 4.5. The samples were withdrawn after 0.25, 0.5, 0.75, 1, 2, 4 hours (hours 2 to 6). Finally, the capsules were inserted into a dissolution bath containing 900 mL of 0.1M Na phosphate buffer, pH 6.8. Samples were taken after 0.25, 0.5, 0.75, 1, 2, 4, 8, and 16 hours (hours 6 to 22). All samples from each pH phase were analyzed for azithromycin using an HPLC method. The average results of the dissolution study of three capsules of each of the CAP and the EUDRAGIT® capsules are shown in FIG. 5.

Figure 5:
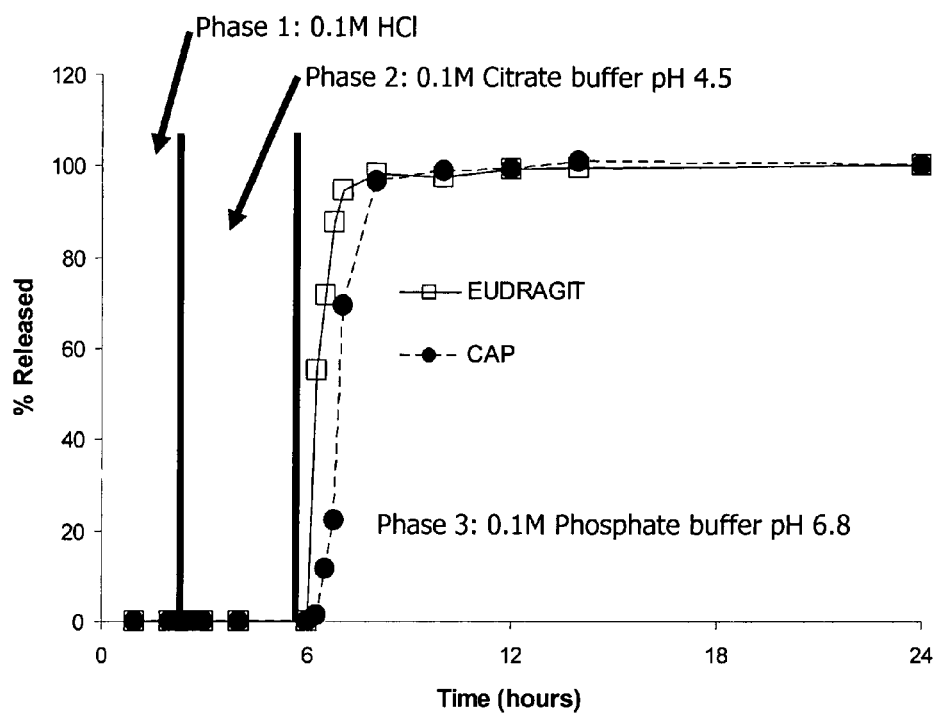
FIG. 5 is a graph showing release profiles of azithromycin from controlled release capsules of the invention coated with different enteric polymers at pH of about 1 (Phase 1), at pH of 4.5 (Phase 2), and at pH of 6.8 (Phase 3).

As shown in FIG. 5, minimal or no release of azithromycin occurred from either the CAP or the EUDRAGIT® capsules at pH of about 1.0 (Phase 1, hours 0 to 2 on FIG. 5) or at pH of 4.5 (Phase 2, hours 2 to 6 on FIG. 5). At pH 6.8 (Phase 3, hours 6 to 22 on FIG. 5), dissolution and release of azithromycin occurred rapidly, with most of the azithromycin being released within one hour.

EXAMPLE 9

Controlled Release Capsule Formulation

Additional controlled release enteric-coated capsules containing 80 mg azithromycin were made using the components shown in Table 8.

TABLE 8

| Component | % w/w |
| --- | --- |
| Azithromycin | 14.55 |
| Sucrose acetate isobutyrate | 36.81 |
| Triacetin | 27.27 |
| Isopropyl myristate | 11.96 |
| Cellulose acetate | 0.85 |
| hydroxyethyl cellulose | 5.13 |
| Silica (Cab-O-Sil ®, Cabot Corp., Billerica, MA) | 2.56 |
| PEG-8 caprylic/capric glyceride (Labrasol ®, Gattefosse, Gennevilliers, France) | 0.85 |
| Butylated hydroxytoluene | 0.02 |
| Total | 100.00 |

The azithromycin release from the controlled release capsules was determined using a triphasic dissolution medium using a USP type II apparatus (paddle) at 100 rpm. The capsules were first immersed in 30 mM citric acid (pH 2.4) and samples were taken at various intervals up to 2 hours. The capsules were then transferred to a second dissolution medium containing sodium phosphate dibasic buffer (pH 4.5). Samples were taken at various intervals up to one hour. Finally, the capsules were inserted into a dissolution medium containing sodium phosphate dibasic buffer (pH 6.2). Samples were taken at various intervals up to 24 hours. All samples were analyzed for azithromycin using an HPLC method. In addition, controlled release capsules were evaluated in a single phase medium of 0.1 mM sodium phosphate buffer (pH 6). Samples were taken at various intervals up to 24 hours. The results of the triphasic and single phase azithromycin release from controlled release capsules are shown in FIG. 6.

Figure 6:
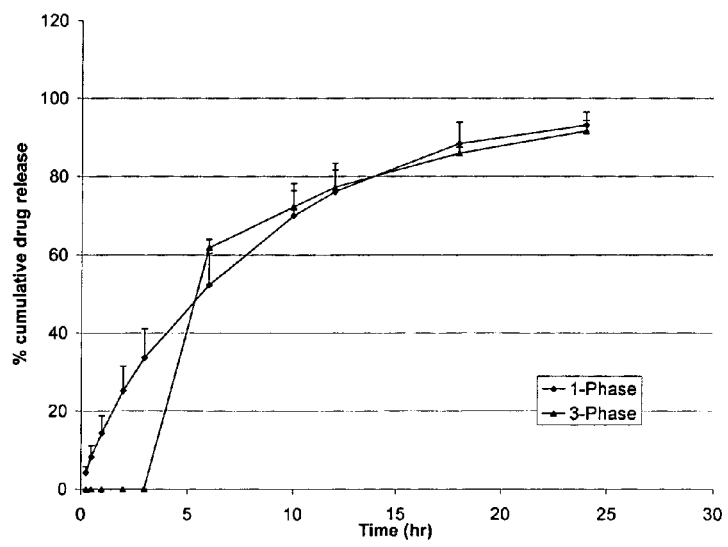
FIG. 6 is a graph showing the release profile of azithromycin from controlled release capsules of the invention exposed to a three phase medium (pH 2.4, pH 4.5, and pH 6.2) and exposed to a single phase medium (pH 6).

As shown in FIG. 6, azithromycin release was not detected in the triphasic study until the capsules were exposed to pH 6.2. FIG. 6 also shows that azithromycin release from the controlled release capsules at pH 6 began essentially immediately and that the release of azithromycin from the capsules was controlled over 24 hours.

While preferred embodiments of the invention have been described in detail, it will be apparent to those skilled in the art that the disclosed embodiments may be modified. It is intended that such modifications be encompassed in the following claims. Therefore, the foregoing description is to be considered to be exemplary rather than limiting, and the scope of the invention is that defined by the following claims.

The invention claimed is:

1. A controlled release solid oral dosage form comprising azithromycin in an amount that is 150 mg or less.

2. The oral dosage form of claim 1 which is a tablet.

3. The oral dosage form of claim 1 which is a capsule.

4. The oral dosage form of claim 1 wherein the amount is 100 mg or less.

5. The oral dosage form of claim 4 wherein the amount is 80 mg or less.

6. The oral dosage form of claim 1 wherein the dosage form is coated with an enteric coating.

7. The oral dosage form of claim 6 wherein the enteric coating includes a methacrylic copolymer.

8. The oral dosage form of claim 1 wherein the dosage form comprises a multiplicity of particles that are individually coated.

9. The oral dosage form of claim 8 wherein the coated particles have been formed into a solid that forms a part of or all of a tablet.

10. The oral dosage form of claim 8 wherein the coated particles are contained within a capsule shell.

11. The oral dosage form of claim 2 that comprises azithromycin, a disintegrating agent, a filler, and binding agent.

12. The oral dosage form of claim 11 which comprises dibasic calcium phosphate, croscarmellose sodium, hydroxypropylmethyl cellulose, and polyethylene glycol.

13. A controlled release solid oral dosage form comprising azithromycin in an amount of 150 mg or less from which dosage form not more than 50% of the azithromycin is released at pH 1 within one hour.

14. The solid oral dosage form of claim 13 from which not more than 25% of the azithromycin is released at pH 1 within one hour.

15. The solid oral dosage form of claim 13 from which not more than 10% of the azithromycin is released at pH 1 within one hour.

16. The solid dosage form of claim 13 which is a tablet.

17. The solid dosage form of claim 13 which is a capsule.

18. The oral dosage form of claim 13 wherein the amount is 100 mg or less.

19. The oral dosage form of claim 18 wherein the amount is 80 mg or less.

20. The oral dosage form of claim 16 that comprises azithromycin, a disintegrating agent, a filler, and binding agent.

21. The oral dosage form of claim 20 which comprises dibasic calcium phosphate, croscarmellose sodium, hydroxypropylmethyl cellulose, and polyethylene glycol.

22. A method for making a solid dosage form for oral administration containing azithromycin comprising combining azithromycin in an amount of 150 mg or less and one or more pharmaceutically acceptable excipients in a solid form and applying an enteric coating to the dosage form.

23. The method of claim 22 wherein the enteric coating is applied to the outer surface of the solid dosage form.

24. The method of claim 23 wherein the enteric coating is applied to individual particles containing azithromycin and the one or more pharmaceutically acceptable excipients within the solid oral dosage form.

25. The method of claim 22 wherein the solid dosage form is a tablet.

26. The method of claim 22 wherein the solid dosage form is a capsule.

27. A method for increasing the bioavailability of azithromycin from an oral solid dosage form containing azithromycin in an amount of 150 mg or less comprising providing said oral dosage form as a controlled release form.

28. The method of claim 27 wherein the oral dosage form is a tablet.

29. The method of claim 27 wherein the oral dosage form is a capsule.

30. The method of claim 27 wherein the amount is 100 mg or less.

31. The method of claim 30 wherein the amount is 80 mg or less.

32. The method of claim 27 wherein the dosage form is coated with an enteric coating.

33. The method of claim 32 wherein the enteric coating includes a methacrylic copolymer.

34. The method of claim 27 wherein the dosage form comprises a multiplicity of particles that are individually coated.

35. The method of claim 34 wherein the coated particles have been formed into a solid that forms a part of or all of a tablet.

36. The method of claim 34 wherein the coated particles are contained within a capsule shell.

37. The method of claim 28 wherein the dosage form comprises azithromycin, a disintegrating agent, a filler, and binding agent.

38. The method of claim 37 wherein the dosage form comprises dibasic calcium phosphate, croscarmellose sodium, hydroxypropylmethyl cellulose, and polyethylene glycol.

39. The oral dosage form of claim 5 wherein the amount is 60 mg.

40. The oral dosage form of claim 19 wherein the amount is 60 mg.

41. The method of claim 22 wherein 100 mg of azithromycin or less is combined.

42. The method of claim 41 wherein 80 mg of azithromycin or less is combined.

43. The method of claim 42 wherein 60 mg of azithromycin is combined.

44. The method of claim 31 wherein the amount is 60 mg.

45. The oral dosage form of claim 5 wherein the amount is 30 mg.

46. The oral dosage form of claim 19 wherein the amount is 30 mg.

47. The method of claim 42 wherein 30 mg of azithromycin is combined.

48. The method of claim 31 wherein the amount is 30 mg.

* * * * *